United States Patent [19]
Jeffers

[11] Patent Number: 5,554,932
[45] Date of Patent: Sep. 10, 1996

[54] MEASUREMENT OF A SATURATION MAGNETIC FLUX DENSITY THROUGH USE OF A ROTATING PERMANENT MAGNET

[75] Inventor: Frederick J. Jeffers, Escondido, Calif.

[73] Assignee: Eastman Kodak Company, Rochester, N.Y.

[21] Appl. No.: 169,082

[22] Filed: Dec. 17, 1993

[51] Int. Cl.[6] .......................... G01N 27/74; G01R 33/12
[52] U.S. Cl. .................. 324/204; 73/53.01; 73/61.42
[58] Field of Search ........................ 324/201, 202, 324/204, 214, 228, 233, 239–243, 226, 262, 71.4; 73/861.08, 861.11, 861.13–861.16, 53.01, 61.42; 340/627, 631

[56] References Cited

U.S. PATENT DOCUMENTS

| | | | |
|---|---|---|---|
| 2,405,137 | 8/1946 | Gale et al. | 324/204 X |
| 2,894,199 | 7/1959 | Kirchner . | |
| 3,777,561 | 12/1973 | Lewis | 73/861.13 |
| 4,187,462 | 2/1980 | Haker et al. | 324/204 |
| 4,243,939 | 1/1981 | Grossman et al. | 324/201 |
| 4,522,501 | 6/1985 | Shannon | 366/142 |
| 4,590,424 | 5/1986 | Girot et al. | 324/204 |
| 4,651,092 | 3/1987 | Brunsch et al. | 324/204 |
| 4,785,239 | 11/1988 | Brunsch et al. | 324/204 |
| 4,808,922 | 2/1989 | Eder et al. | 324/204 |
| 5,001,424 | 3/1991 | Kellett et al. | 324/204 |
| 5,089,781 | 2/1992 | Arichika et al. | 324/204 X |
| 5,287,056 | 2/1994 | Jackson et al. | 324/239 |

FOREIGN PATENT DOCUMENTS

| | | | |
|---|---|---|---|
| 0970288 | 10/1982 | U.S.S.R. | 324/204 |
| 0995035 | 2/1983 | U.S.S.R. | 324/204 |
| 1126859 | 11/1984 | U.S.S.R. | 324/204 |
| 1383239 | 3/1988 | U.S.S.R. | 324/204 |

OTHER PUBLICATIONS

LDJ Inc., *The Model 7600A Microprocessor Controlled BH Meter* (Date not available).
LDJ Inc., *The LDJ Model 7000B BH Meter*, (date not available).

*Primary Examiner*—Sandra L. O'Shea
*Assistant Examiner*—Jay M. Patidar
*Attorney, Agent, or Firm*—William F. Noval

[57] ABSTRACT

In order to measure the magnetic saturation flux density of a sample material, a first and a second sample holder are symmetrically position on either side of a cylindrical permanent magnet. Coils are placed around the sample holders and the permanent magnet is rotated. The signals induced in the coils in the absence of a magnetic material in one of the sample holders are applied to an amplifier/meter in such a manner as to provide a null signal. When a sample is placed in one of the sample holders, the magnetic saturation flux density can be measured. The present device finds particular application to determining the concentration of a magnetic particles dispersed in a fluid.

19 Claims, 1 Drawing Sheet

MEASUREMENT OF A SATURATION MAGNETIC FLUX DENSITY THROUGH USE OF A ROTATING PERMANENT MAGNET

FIELD OF THE INVENTION

This invention relates generally to the measurement of magnetic properties of a material and, more particularly, to providing a measurement of magnetic properties relevant to magnetic particles dispersed in a non-magnetic medium.

BACKGROUND OF THE INVENTION

In a non-magnetic medium, such as a fluid, in which magnetic particles are dispersed, a measurement of the magnetic properties has been used to determine parameters such as the magnetic particle concentration in the medium. In the prior art, the response of the medium to the application of a magnetic field to a magnetic particle-bearing fluid has been used to measure the properties of magnetic particles suspended therein and, consequently, to determine the properties of fluid itself. In U.S. Pat. No. 4,651,092, entitled, METHOD OF DETERMINING DISPERSION OF VISCOSITY OF RESIN/SOLVENT MIXTURE CONTAINING MAGNETIC PARTICLES, issued on Mar. 17, 1987 in the name of A. Brunsch et al., a magnetic field generated by a set of coils is applied to fluid to determine characteristics of magnetic particles suspended in a fluid medium, for example, the concentration of magnetic particles in the medium. In the configuration disclosed, a relatively small magnetic field (approximately 10 Oe) is generated. In U.S. Pat. No. 4,522,501, entitled MONITORING MAGNETICALLY PERMEABLE PARTICLES IN ADMIXTURE WITH A FLUID CARRIER, issued on Jun. 11, 1985 in the name of M. A. Shannon, the concentration of magnetic particles in a fluid medium is determined by measuring the change in torque in a rotating conducting member resulting from the eddy current variation when the fluid medium is used to shield the rotating member from a magnetic field. Neither of the references provides sufficient accuracy for the determination of the magnetic properties of the magnetic medium.

Apparatus is commercially available for measuring the magnetic properties of a material. For example, Model 7600A BH Meter available from LDJ Incorporated is a microprocessor-controlled device designed to measure magnetic properties of materials. Such devices are both expensive and bulky and can typically measure parameters which, in many situations, are not important for the characterization of the material.

A need has therefore been felt for apparatus and an associated method for measuring the dispersion or the magnetic saturation of a fluid having magnetic particles suspended therein, the apparatus selected being relatively simple, accurate, and which does not involve undue complication.

SUMMARY OF THE INVENTION

The present invention is directed to overcoming one or more of the problems set forth above. Briefly summarized, according to one aspect of the present invention, a cylindrical permanent magnet which is caused to physically rotate, has a sample coil and a reference coil symmetrically disposed with respect to the axis of the cylindrical magnet, the coils being positioned on opposite sides of the permanent magnet axis. The sample coil surrounds a sample holder in which a material sample can be placed. The reference coil and the sample coil, in the absence of a magnetic material interacting with the rotating field, can be adjusted to provide a null signal when applied to the input terminals of an amplifier/meter. When a material sample is placed in the material sample holder, the magnetic particles of the material interact with the changing magnetic field resulting from the rotation of the permanent magnet. A voltage is generated as a result of the interaction of the material sample with the changing magnetic field. The voltage can be used to determine the saturation flux of the material and, consequently, the concentration of magnetic particles in the material. By flowing a fluid material sample through the sample holder, the apparatus can be used in process control applications.

The present invention advantageously provides for an accurate saturation flux measurement without the use of elaborate apparatus. This measurement can provide the concentration of magnetic particles in the material. The configuration is suitable for use as a portion of a process control system.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 1a is a side view schematic block diagram of the configuration used in determining the magnetic properties of a sample of magnetic material positioned in one of two coils symmetrically positioned on opposite sides of a cylindrical magnet, while

DETAILED DESCRIPTION OF THE INVENTION

Figure 1A:
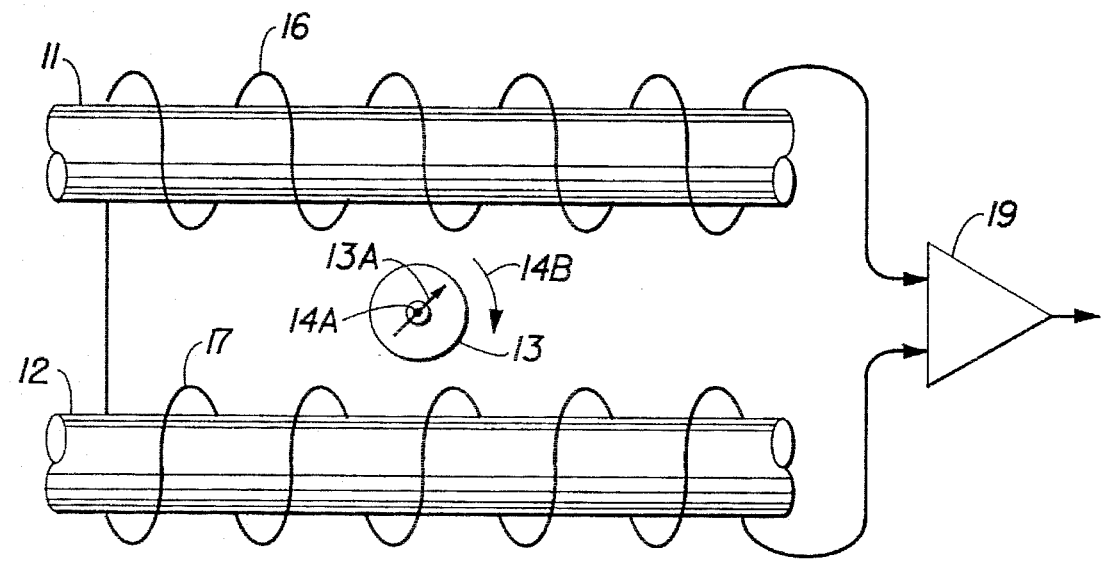
Figure 1B:
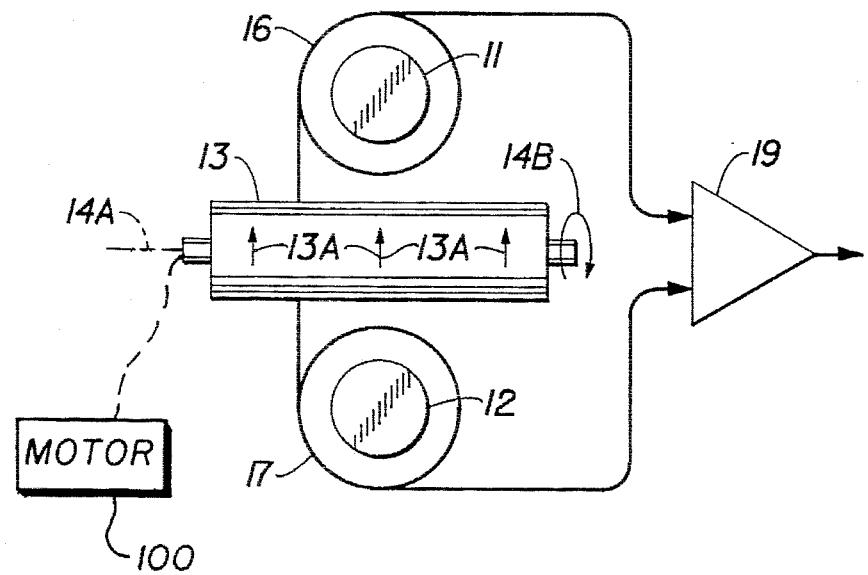
FIG. 1b is an end view schematic block diagram of the configuration.

Referring to FIG. 1, a cylindrical permanent magnet 13 has an axis of magnetization in a direction indicated by the arrow 13A, i.e., perpendicular to the axis of the cylindrical magnet. The cylindrical permanent magnet is rotated by motor 100 (FIG. 2) about an axis 14A in a direction indicated by the arrow 14B. Sample holders 11 and 12 are symmetrically positioned with respect to the cylindrical magnet 13 on opposite sides of the magnet. Each sample holder has an axis positioned in a plane perpendicular to the axis of rotation 14A. Sample holder 11 has coil 16 wrapped there around, while sample holder 12 has coil 17 wrapped there around. The coils 16 and 17 are coupled so that voltages induced therein by the changing magnetic field (i.e., from rotating cylindrical permanent magnet 13) are in opposition. The coils are coupled in series and applied to input terminals of amplifier/meter 19. Typically, the coils 16 and 17 are arranged so that, in the absence of a sample material, no voltage signal is applied to amplifier 19.

When a magnetic material is placed in one of the sample holders, the changing magnetic field from the rotating cylindrical permanent magnet 13 causes the magnetic material to generate a (changing) magnetic flux. The changing magnetic flux induces a voltage in the associated coil which is not duplicated in the other coil. Consequently, the signals induced in the coils are no longer balanced and a voltage is present on the output terminal of amplifier/meter 19.

In a preferred embodiment, the rotating magnet B-H meter is used to measure the pigment concentration or saturation magnetization of a coating material. The magnet is 1.5 inches in diameter by 2.0 inches long and is fabricated from an NdFeB material. The magnet has a field of approximately 2400 Oe which is selected to insure saturation of the 900 Oe coercivity particles in the coating material. An ⅛ horsepower motor rotates the permanent magnet at 3,600 RPM so that the field frequency is 60 Hz. The windings in the coils 16 and 17 each have 1,000 turns. With no sample material in the device, the primary voltages induced in the coils will cancel. In operation, the coating material is placed in the sample holder associated with one of the coils. The magnetic field from the permanent magnet magnetizes the coating material and the voltage induced in the coil will be proportional to the time rate of change of the resultant magnetic flux. Because the field from the magnet is a large rotating vector, for which the magnitude of 2,500 Oe is much larger than the 900 Oe coercivity of the sample, the magnetization of the media being measured is saturated parallel to the field from the magnet. Hence, the magnetization is a constant rotating vector and thus the voltages induced in the coils are sine waves. The magnitude of the voltage is proportional to the saturation flux density of the sample. The 60 Hz sine wave signal amplitude generated by a flux magnitude of 1 Maxwell is about 65 mV, a signal which can be detected with a signal to noise ratio of approximately 30 dB. Electronic integration can give the saturation flux density of the coating material. Calibration can be performed by inserting a standard material into the second sample holder.

It will be now appreciated that there has been presented apparatus and method for measuring the saturation flux density of a sample medium. It will be clear that the sample holder can be a tube and that the medium can flow continuously through the tube. In this manner, the present apparatus can be used to monitor continuously the fluid flowing through the sample holder and can be incorporated as part of a process control system. In the process control system, the concentration of magnetic particles can be continuously monitored and appropriate adjustments performed as a result of the measurements.

Operation of the present invention is believed to be apparent from the foregoing description and drawings, but a few words will be added for emphasis. The disclosed apparatus is particularly useful in the determination of the properties of materials into which magnetic particles have been dispersed. The disposed apparatus uses relatively simple and relatively inexpensive apparatus while providing an accurate measurement of the saturation flux density.

While the invention has been described with reference to a fluid medium, it is apparent that the invention is easily adapted to the insertion of nearly any magnetic material in the sample holder. As long as the effective coercivity of the magnetic material is smaller than the 2500 Oe field from the rotating permanent magnet, the signal induced will be a simple sine wave and electronic integration to obtain the saturation flux density is not required. If high coercivity samples are measured, electronic integration may be needed.

While the invention has been described with particular reference to a preferred embodiment, it will be understood by those skilled in the art that various changes may be made and equivalents may be substituted for elements of the preferred embodiment without departing from invention. In addition, many modifications may be made to adapt a particular situation and material to a teaching of the invention without departing from the essential teachings of the present invention.

As is evident from the foregoing description, certain aspects of the invention are not limited to the particular details of the examples illustrated, and it is therefore contemplated that other modifications and applications will occur to those skilled in the art. It is accordingly intended that the claims shall cover all such modifications and applications as do not depart from the true spirit and scope of the invention.

PARTS LIST

11 first sample holder
12 second sample holder
13 cylindrical permanent magnet
13A direction of magnetization of the permanent magnet
14A axis of rotation of the permanent magnet
14B direction of rotation of the permanent magnet
16 coil surrounding the first sample holder
17 coil surrounding the second sample holder
19 amplifier/meter

What is claimed is:

1. A device for measuring the magnetic properties of a material, said device comprising:

a radially magnetized dipole permanent cylindrical magnet having a cylindrical axis and having an axis of magnetization perpendicular to and passing through said cylindrical axis;

rotational apparatus for rotating said magnet about a cylindrical axis;

first and second sample holders;

a first inductive pick-up coil wrapped around said first sample holder and positioned on a first side of said magnet, said first coil and first sample holder having an axis in a plane perpendicular to said cylindrical axis; and a second inductive pickup coil wrapped around said second sample holder and having a symmetric position with respect to said first coil on the opposite side of said cylindrical axis, said first and second coils being electrically coupled; wherein rotation of said dipole permanent magnet produces changing magnetic field which induces opposite voltages in said coils which cancel leach other when no sample material is disposed in said first sample holders, but which produces unbalanced voltages in said coils which result in a net voltage which is a measure of a magnetic property of said sample material disposed in said first sample holder.

2. The device of claim 1 wherein said sample material to be tested produces a voltage in said first coil proportional to the time rate of change of magnetic flux produced in said material to be tested by said rotating permanent magnet.

3. The device of claim 2 wherein the voltage produced in said first coil determines said magnetic property of said material to be tested.

4. The device of claim 2 wherein the voltage produced in said first coil is approximately a simple sine wave having an amplitude which is proportional to the magnetic property of said material to be tested.

5. The device of claim 1 wherein said sample material is a fluid, said fluid flowing through said first sample holder and first coil.

6. The device of claim 5 wherein said induced voltages are combined to provide a monitoring signal, said monitoring signal determining at least one magnetic parameter of said material.

7. The device of claim 1 wherein said device is calibrated by placing a sample with at least one predetermined magnetic property in one of said coils and a standard in the other of said coils.

8. A method of determining magnetic properties of a sample material, said method comprising the steps of:

placing said sample material in a first sample holder surrounded by a first inductive pick-up coil;

positioning a rotating cylindrical radially magnetized dipole permanent magnet in a position proximate said first inductive pick-up coil wherein said rotating magnet has a cylindrical axis of rotation and has an axis of magnetization perpendicular to and passing through said cylindrical axis;

positioning a second sample holder surrounded by a second inductive pick-up coil in a symmetrical position on an opposite side of said rotating cylindrical dipole permanent magnet; and electrically coupling said first and said second inductive pick-up coil to provide a substantially null signal in the absence of said sample material.

9. The method of claim 8 further including the step of selecting said second inductive pick-up coil to be substantially identical to said first pick-up coil.

10. The method of claim 8 further including the step of placing a standard material with at least one predetermined magnetic property in said second sample holder to calibrate an output signal provided by combining induced signals from said first and second inductive pick-up coils.

11. The method of claim 8 wherein said sample material is a fluid, said method further comprising the step of measuring an output signal from said first inductive pick-up coil when said fluid is flowing through said first sample holder.

12. The method of claim 8 wherein said sample material has a saturation flux density characteristic and further including the step of determining the saturation flux density of said material to be tested, said saturation flux density of the material to be tested being proportional to an amplitude of a signal induced in said first inductive pick-up coil when said signal is a simple sine wave.

13. Apparatus for measuring at least one magnetic parameter of a material, said apparatus comprising:

a first sample holder for holding a sample material to be tested;

a first coil surrounding said first sample holder;

a radially magnetized dipole cylindrical permanent magnet polarized perpendicularly to and passing through the geometric axis of rotation of said cylindrical permanent magnet, wherein said first coil has an axis in a plane perpendicular to said permanent magnet geometric axis of rotation;

a second sample holder;

a second coil surrounding said second sample holder wherein said second sample holder and said second coil are positioned on an opposite side of said permanent magnet from said first sample holder and said coil and symmetric with respect to said first sample holder and said first coil; and apparatus for rotating said cylindrical permanent magnet about said permanent magnet geometric axis to induce voltages in said first and second coils, wherein said first and said second coils are electrically coupled to provide a zero output voltage when a sample of said material is not placed in said first sample holder.

14. The apparatus of claim 13 wherein said apparatus can be calibrated by placing a sample of a material having a predetermined magnetic parameter in said first sample holder and a standard in said second sample holder.

15. The apparatus of claim 13 wherein said material is a fluid, said first sample holder being a tube through which said fluid flows.

16. The apparatus of claim 13 wherein output signals from said first and said second coils determine a saturation flux density for said material.

17. The apparatus of claim 16 wherein said saturation flux density can be integrated to provide a magnetic flux induced in said material by said rotating permanent magnet.

18. The apparatus of claim 13 wherein said sample material has a saturation flux density characteristic and wherein an amplitude of the voltage induced in said first coil is proportional to the saturation flux density of the material to be tested when said voltage induced in said first coil is a sine wave.

19. The apparatus of claim 13 wherein the combined output signals from said first and said second coils are approximately simple sine waves having an amplitude, wherein said sample material has a saturation flux density characteristic, and wherein, the amplitude of output signals being proportional to the saturation flux density of the material to be tested.

* * * * *